United States Patent
Altabet

(10) Patent No.: US 6,943,193 B1
(45) Date of Patent: Sep. 13, 2005

(54) METHOD FOR TREATING SEXUAL DYSFUNCTION

(76) Inventor: Jordan A. Altabet, 7770 Regents Rd., Unit #113-517, San Diego, CA (US) 92122

( * ) Notice: Subject to any disclaimer, the term of this patent is extended or adjusted under 35 U.S.C. 154(b) by 0 days.

(21) Appl. No.: 10/750,743

(22) Filed: Jan. 3, 2004

Related U.S. Application Data

(60) Provisional application No. 60/441,247, filed on Jan. 21, 2003.

(51) Int. Cl.[7] ........................ A61K 31/35; C07C 217/54

(52) U.S. Cl. ........................................ 514/561; 564/347
(58) Field of Search .......................... 564/347; 514/651

(56) References Cited

U.S. PATENT DOCUMENTS

| | | | |
|---|---|---|---|
| 6,184,222 B1 * | 2/2001 | Heiligenstein | 514/239.2 |
| 2002/0010216 A1 * | 1/2002 | Rogosky et al. | 514/649 |

* cited by examiner

*Primary Examiner*—Brian Davis

(57) ABSTRACT

Treatment of sexual dysfunction disorders comprising administering an effective amount of atomoxetine.

14 Claims, No Drawings

METHOD FOR TREATING SEXUAL DYSFUNCTION

RELATED APPLICATION/CLAIM OF PRIORITY

This application is related to and claims priority from Provisional Application Ser. No. 60/441,247, filed Jan. 21, 2003.

I. BACKGROUND OF THE INVENTION

1. Field of the Invention

This invention relates to the treatment sexual dysfunction, particularly sexual desire, arousal, orgasmic and premature ejaculation disorders.

2. Background

Atomoxetine HCl has been the subject of clinical studies for the treatment of Attention Deficit Hyperactivity Disorder (ADHD) and has received FDA approval as the prescription drug Strattera™ (Eli Lilly and Company) for the treatment of ADHD in Nov. 2002. Atomoxetine, originally named tomoxetine, is a selective norepinephrine reuptake inhibitor. Tomoxetine was first disclosed in U.S. Pat. No. 4,314,081. Tomoxetine is also disclosed in U.S. Pat. No. 6,184,222 as a treatment for conduct disorder. The word "atomoxetine" will be used herein to refer to any acid addition salt or the free base of the molecule.

The regulation of norepinephrine and dopamine plays a crucial role in our mental and physical health.

Dopamine agonists have been administered to treat various disorders of sexual dysfunction. Apomorphine, a direct acting dopamine agonist, has demonstrated an erectogenic effect in human subjects. Several other direct acting dopamine agonists such as bromocriptine, quinelorane, lisuride and pergolide that have been discussed in the related art, have had limited efficacy in treating sexual dysfunction.

Other drugs have been introduced in an attempted to treat sexual dysfunction. They include administering amantadine, buspirone, cyproheptadine, phentolamine and yohimbine. These attempts at pharmaceutical intervention have also demonstrated limited efficacy.

Viagra™ (sildenafil: a phosphodiesterase 5 inhibitor) has been used successfully in the treatment of erectile dysfunction. Since phosphodiesterase 5 (PDE 5) inhibitors have demonstrated substantial efficacy, an abundance of research has been directed toward the treatment of erectile dysfunction by way of the PDE 5 mechanism. Consequently, product development research for the treatment of the other disorders of sexual dysfunction (i.e., sexual desire or orgasmic disorders in both men and women) has been minimal when compared to research pertaining to erectile dysfunction.

The FDA has provided guidance recommendations for clinical development of drug products for the treatment of female sexual dysfunction (FSD). FSD currently consists of four recognized components: decreased sexual desire, decreased sexual arousal, persistent difficulty in achieving or inability to achieve orgasm and dyspareunia. Commentary by numerous treatment centers and pharmaceutical companies to the FDA's guidance stressed that decreased desire is the most predominant factor that needs to be addressed regarding FSD. Research has begun to develop therapeutics to treat female vasculogenic impairment as it relates to sexual arousal disorders. However, development of effective treatments for psychogenic and other organic etiologies of FSD has been minimal.

Emotional problems and changes in sexual desire are almost always associated with each other. However, changes in sexual desire without associated emotional problems or organic abnormalities are relatively common. Therefore, sexual desire disorders appear to be a core problem with which other disorders of sexual dysfunction may overlap. Therefore, there is a continued need to develop effective pharmaceutical treatment for sexual dysfunction that manifests from a decrease or absence of sexual desire.

In view of the aforementioned deficiencies attendant with the related art, the need still exists for rapid, reliable, and convenient method for treating sexual dysfunction suitable for men and women.

II. SUMMARY OF THE INVENTION

The present invention provides a method for treating sexual dysfunction in men and women comprising administration of a therapeutically effective amount of atomoxetine or pharmaceutically acceptable salt thereof.

The invention provides a method for treating sexual dysfunction in patients with symptoms including: decreased or absent sexual desire; persistent difficulty in achieving or inability to achieve orgasm; decreased or absent sexual arousal; premature ejaculation; and dyspareunia.

It is an objective of this invention to treat disorders of sexual dysfunction that are described in the Diagnostic and Statistical Manual of Mental Disorders, 4th edition, (DSM-IV), Washington D.C., American Psychiatric Association, 1996 (incorporated herein by reference). These disorders include: hypoactive sexual desire disorder and sexual aversion disorder; female sexual arousal disorder and male erectile disorder; female orgasmic disorder and male orgasmic disorder; premature ejaculation and dyspareunia. Sexual dysfunction due to a general medical condition or substance induced is also included. The scope of application of this invention includes all DSM-IV subtypes of these disorders. These subtypes are lifelong, acquired, generalized and situational.

Terminology

Desire refers to fantasies about sexual activity and the desire to have sexual activity.

Arousal refers to the subjective sense of sexual pleasure and accompanying physiological changes. The major changes in the male consist of penile tumescence and erection. The major changes in the female consist of vasocongestion in the pelvis, vagina lubrication and expansion, and swelling of the external genitalia.

Orgasm refers to the highest point of sexual excitement characterized by a subjective experience of intense pleasure marked normally by ejaculation in the male and vaginal contractions in the female.

Treatment or to "treat" refers to both treatment and to prophylactic therapy or prevention.

Organic: Of, relating to, or affecting organs or an organ of the body including a physiologic change due to a general medical condition.

Psychogenic: Originating in the mind or in a mental or emotional process; psychological. For the purposes of this invention, disorders of psychogenic origin as stated herein are defined as disorders with no apparent overwhelming organic basis. An example of disorders with an overwhelmingly organic basis are disorders that may require surgery or medication to remedy a physical impediment restricting blood flow to the genitalia.

III. DETAILED DESCRIPTION OF THE INVENTION

The present invention provides a method for treating sexual dysfunction in men and women comprising administration of a therapeutically effective amount of atomoxetine or pharmaceutically acceptable salt thereof.

Sexuality is a complex process coordinated by neurological, vascular, endocrine and cortical events. Treatment of sexual dysfunction includes psychosexual counseling, and when appropriate, pharmaceutical augmentation.

It is recognized that the dopaminergic system facilitates sexual activity. However, humans are a uniquely cognitive species. Sexuality, in part, can be identified with the frontal lobes of the brain. This psychological component is equally as important as the physiological mechanisms of sexual health. There is cortical physiologic activity that occurs in relation to the sexual response, which has considerable influence on desire, arousal and orgasm in men and women.

The central nervous system functions of norepinephrine have been linked to cognitive functions associated with the frontal lobes in the regulation of alertness, maintenance of selective attention, the cognitive treatment of information, and retarding of cerebral aging. Deficits in cognitive performance can be reversed with noradrenergic agonists. Conversely, distractibility is magnified whenever noradrenergic activity is reduced. Additionally, with regard to mood, it is now believed the most important pathways are those of the noradrenergic neurons projecting to the prefrontal cortex. Therefore, the inventor believes that a possible mechanism by which atomoxetine produces its therapeutic effect in the treatment of sexual dysfunction is related to selective inhibition of pre-synaptic norepinephrine transporter in these areas of the central nervous system.

A preferred embodiment of this invention is the administration of a therapeutically effective amount of atomoxetine HCl to treat sexual dysfunction. Atomoxetine HCl is a selective norepinephrine reuptake inhibitor. The chemical designation is (−)—N-Methyl-3-phenyl-3-(o-tolyloxy)-propylamine hydrochloride.

Another preferred embodiment of this invention provides a method of treatment comprising administration of the lowest dosage of atomoxetine that will provide relief of the targeted sexual dysfunction disorder.

Benefits

A major advantage of this invention is that it provides for the administration of a single pharmaceutical compound to treat certain types of sexual dysfunction in both men and women.

However, when indicated, pharmaceutical combinations with atomoxetine are important augmentations to treatment. Combined treatment with atomoxetine and sexual therapeutics with a different mechanism of action (i.e., sildenafil, alprostadil, phentolamine, etc.) may be more effective in reversing sexual disorders such as erectile dysfunction when multifactorial causes exist.

Atomoxetine provides a lower risk of sleep disturbances, such as insomnia, when compared to certain therapeutics administered to treat sexual dysfunction.

Atomoxetine has been used safely in adult and child clinical studies for the FDA approved treatment of ADHD. Generally, atomoxetine will be administered to treat sexual dysfunction in doses equal to or lower than that administered as treatment for ADHD. This comparison provides an indication of the safety of atomoxetine for use in treating sexual dysfunction.

TREATMENT EMBODIMENTS OF THIS INVENTION

Atomoxetine can be administered alone or in conjunction with counseling and other therapeutic agents to treat the following disorders:

Hypoactive Sexual Desire Disorder

The essential feature of hypoactive sexual desire disorder is a deficiency or absence of sexual fantasies and desire for sexual activity. Low sexual desire may encompass all forms of sexual expression or may be limited to a specific sexual activity (i.e., intercourse but not masturbation). There is little motivation to seek stimuli to diminish frustration when deprived of the opportunity for sexual expression. The individual usually does not initiate sexual activity or may only engage in it reluctantly when it is initiated by the partner. Hypoactive sexual desire disorder includes female and male desire disorders.

Hypoactive sexual desire disorder is often a core problem with which other sexual problems may overlap, and therefore, is a factor that may need to be addressed when treating other disorders of sexual dysfunction.

Sexual aversion disorder is an aversion to and active avoidance of genital sexual contact with a sexual partner. Because of certain similarities to hypoactive sexual desire disorder, sexual aversion disorder is often treated in a similar manner.

Erectile Disfunction (Male Erectile Disorder)

Erectile dysfunction is defined as a persistent or recurrent inability to attain, or to maintain until completion of the sexual activity, an adequate erection. An erection is the result of psychogenic and local stimulation. Generally, erectile dysfunction may result from psychogenic disturbances, organic abnormalities, or a combination of both. Psychogenic factors are the most common cause of erectile dysfunction.

Atomoxetine can be administered alone or conjunction with erectogenic agents to treat erectile dysfunction. The following are examples of erectogenic agents:

Although initial reports indicated success rates as high as 85% clinical practice has shown the efficacy of sildenafil (Viagra™) to be closer to 50%. Sildenafil acts by inhibiting phosphodiesterase 5, found primarily within the corpora cavernosa. This inhibition results in increased cGMP concentration, thus increasing smooth muscle relaxation and erection. However, sildenafil is not involved in the generation of cGMP, which explains why the drug can augment erection but not cause one to occur by itself. Sildenafil does not impact directly on desire or orgasm.

Another erectogenic agent is yohimbine. Aphrodyne™ (yohimbine hydrochloride), an indolalkylamine alkaloid with chemical similarity to reserpine, blocks presynaptic alpha-2-adrenergic receptors. Yohimbine affects the peripheral autonomic nervous system to increase cholinergic (parasympathetic activity) and decrease adrenergic (sympathetic activity). Male erection is linked to cholinergic activity and to alpha-2-adrenergic blockade which may result in increased penile inflow of blood and decreased penile outflow or both. A modest reversal of erectile dysfunction has been attributed to treatment with yohimbine.

Phentolamine (Vasomax) is an α-adrenergic vasodilator that can be administered to treat circulatory problems related to blood flow to male genitalia.

Female Sexual Arousal Disorder

Female sexual dysfunction has not been studied as extensively as male sexual dysfunction. It is known that in women sexual arousal is accompanied by arterial inflow, which engorges the vagina and increases vaginal lubrication. The essential feature of Female Sexual Arousal Disorder is a persistent or recurrent inability to attain, or maintain until the completion of sexual activity, an adequate lubrication-swelling response of sexual excitement.

Dyspareunia, either superficial or vaginal, is often caused by friction (i.e., lubrication problems), which may originate from arousal disorders.

Male Orgasmic Disorder

Male orgasmic disorder is the persistent or recurrent delay in orgasm or absence of orgasm following a period of normal sexual arousal. Retarded ejaculation refers to male coital anorgasmia, which is also classified under this disorder.

Female Orgasmic Disorder

The diagnostic criteria for female orgasmic disorder describe a persistent or recurrent delay in orgasm or absence of orgasm following a period of normal sexual arousal. As with other sexual dysfunction disorders it should be determined if the orgasmic disorder is caused by sexual inexperience or the lack of adequate stimulation. In such instances, relief may only require sex therapy and sex education.

Premature Ejaculation

The essential feature of premature ejaculation is the persistent or recurrent onset of orgasm and ejaculation with minimal stimulation before, on, or shortly after penetration.

Medical Conditions

The present invention provides a method for treating sexual dysfunction resulting from a general medical condition or a combination of medical conditions.

Substances

The present invention provides a method for treating sexual dysfunction induced by substances, which include medications prescribed for other conditions. The consequences of sexual dysfunction induced by medication are significant and can result in patients not complying with drug therapy, leading to relapse in the treated disease or symptoms. It would be highly beneficial in promoting patient compliance if pharmaceutical compositions could be administered without the unwanted side effects of sexual dysfunction.

Formulation and Delivery Method

This invention comprises formulations and delivery methods for atomoxetine where a therapeutically effective amount can be administered for the treatment of sexual dysfunction using a variety of preparations. Oral administration is the preferred method of delivery and can be in the form of a tablet, capsule, liquid, or food additive. Preparations for sublingual, buccal and nasal administration are the methods of choice when rapid delivery to the blood stream is desired.

A preferred embodiment of this invention is the administration of a therapeutically effective amount of atomoxetine in the hydrochloride salt form atomoxetine HCl to treat sexual dysfunction. The chemical designation is (−)—N-Methyl-3-phenyl-3-(o-tolyloxy)-propylamine hydrochloride. Atomoxetine HCL or other pharmaceutically acceptable salt forms are preferred embodiments of this invention.

This invention provides that the formulation comprises about 5% to about 95% atomoxetine. Formulations can include one or more of the salt forms.

This invention further provides that it is preferable to present atomoxetine as a pharmaceutical formulation with an acceptable carrier where atomoxetine comprises about 5% to 95% by weight of the formulation.

The carrier should be acceptable in the sense of being compatible with the other ingredients of the formulation and not deleterious to the recipient thereof.

The formulations may conveniently be presented in unit dosage form and may be prepared by any of the methods well known in the art of pharmacy.

Other formulations of the present invention suitable for oral administration may be presented as discrete units such as capsules, tablets or lozenges, microencapsulated or time-release forms; or as a suspension or solution in a liquid such as a syrup, an elixir, or an emulsion.

The invention further provides that the carrier may have a time release mechanism, which may be prepared by any of the methods well known in the art of pharmacy. An advantage of the time release mechanism over other delivery methods is that it can reduce the daily effective dosage of atomoxetine and maintain consistent blood levels of atomoxetine. This mechanism will help moderate peak blood concentrations, which can enhance the therapeutic result.

This invention also provides a method for accelerating the rate of delivery of atomoxetine by administration topically in the mouth (for example sublingually or buccally). Topical administration generally improves the rate of delivery to the systemic circulation. As a result, the time for the initial onset of the therapeutic effect can decrease significantly and the dose required may be less than when administered by ingestion.

Formulations suitable for topical administration of atomoxetine include lozenges comprising a flavored basis such as sucrose and acacia, and pastilles comprising a basis such as gelatin and glycerin or sucrose and acacia.

This invention also provides for administration by nasal, transdermal (i.e. skin patch), percutaneous, intravenous, intramuscular or intrarectal delivery methods. Formulations for these delivery methods may be prepared by any of the methods well known in the art of pharmacy.

Above are examples of appropriate formulations for delivery of this invention and are not meant to exclude other methods of delivery.

Any of the pharmaceutical formulations described above may be presented in a conventional manner associated with controlled release forms.

Dosage

Therapeutic levels of atomoxetine may be obtained with a unit dose as low as 10 mg of atomoxetine. Preferably, a therapeutically effective unit dose will range from about 10 mg to about 100 mg of atomoxetine, though a total daily dosage of more than 100 mg may be required. Atomoxetine may be administered in one or more unit doses.

The unit dose of atomoxetine for oral administration will preferably contain about 10 mg to about 100 mg of atomoxetine, which can be administered, for example, once or twice daily or as needed.

Dosage parameters of atomoxetine for sublingual or buccal administration are similar to those for oral administration. The unit dose of atomoxetine for these routes of administration will preferably contain about 10 mg to about 100 mg of atomoxetine, which can be administered, for example, once or twice daily or as needed.

The specific unit dose, total daily dosage and duration of treatment will vary depending upon the particular patient. The precise unit dose administered will depend on the age and condition of the patient, the particular compound used and the frequency and route of administration and will ultimately be at the discretion of the attendant physician.

Combination Delivery

Atomoxetine may be administered in combination with one or more therapeutic agents such as estrogen or estrogen/androgen replacement agents, hypnotic, antidepressant or anti anxiety agents, anti-cancer agents, or in combination with a course of therapy such as radiation therapy to treat cancer. Atomoxetine formulations of this invention may also include other therapeutic agents used in the treatment of sexual dysfunction. Examples of these therapeutic agents are sildenafil, phentolamine, yohimbine and apomorphine.

These novel combinations may be conveniently presented for use in the form of a pharmaceutical formulation comprising atomoxetine together with at least one other therapeutic agent and one or more pharmaceutically acceptable carriers and shall comprise a further aspect of the invention. Additionally, this invention provides that atomoxetine and the therapeutic agent may be administered either sequentially or simultaneously by any convenient delivery method.

The novel combination comprises an amount of therapeutic agent sufficient to alleviate the agent's targeted disorder, disease or symptoms, and an amount of atomoxetine sufficient to eliminate or reduce sexual dysfunction. Treatment may be further augmented with atomoxetine that has not been combined with a therapeutic agent. Standard methods of preparation for pharmaceutical combinations are used. Usually when such combinations are employed the dose of each therapeutic agent in the combination will approximate that employed for each agent when used alone. The therapeutic agent/atomoxetine combination must be compatible in order to produce the desired treatment results and must be safe for patient use (for example, atomoxetine should not be combined or taken in conjunction with monoamine oxidase inhibitors).

One convenient form for administering the inventive combination is in the form of tablets or capsules to be taken orally. The therapeutic combination may be formulated for other routes of administration. The therapeutic combination may be dispensed in time release form.

Therapeutic agents that can be combined with atomoxetine, or administered sequentially or simultaneously with atomoxetine include:

1. Phosphodiesterase inhibitors, including phosphodiesterase 5 inhibitors such as Viagra™ (Pfizer), Cialis™ (Lilly, Icos), Vardenafil™ (Bayer).

2. Prostaglandin formulations such as Alprox™ and Femprox™ (both contain alprostadil and are NexMed products). Alprostadil is a vasodilator recognized for treating erectile dysfunction that is applied to the genital area. Clinical data indicates that Femprox™ offers potential as a promising treatment for improving blood flow to the genital area of females restoring engorgement and lubrication to help relieve symptoms of FSAD.

3. Cyproheptadine or other serotonin antagonists.

4. Methyltestosterone (Virilon™—Star Pharmaceuticals) or other hormone replacement agents.

5. Apomorphine, amantadine, bromocriptine, deprenyl, lisuride, pergolide or other dopamine agonists.

6. Yohimbine, phenoxybenzamine, phentolamine, delaquamine, ergot alkaloids, or other adrenergic antagonists.

7. Finasteride (Propecia™), an inhibitor of Type II 5a-reductase, or other hair growth agents.

8. Adrenergic agonists, diuretics, anticholinergics, cholinergic agonists, antipsychotics, antidepressants, anxiolytics, hormone therapies and chemotherapeutics.

The therapeutics and classes of therapeutics listed above represent only a sample of therapeutics that may be combined with atomoxetine or administered either sequentially or simultaneously with atomoxetine and are not intended to limit the scope of this invention.

TREATMENT EXAMPLES

Menopause/Post Menopause

Atomoxetine can be administered alone, or in combination with estrogen or estrogen/androgen replacement therapy as treatment to alleviate sexual dysfunction secondary to menopause. Combination therapy may provide greater efficacy in the treatment of these sexual disorders than that provided by hormone replacement alone.

Breast Cancer and Estrogen

Women who are postmenopausal at breast cancer diagnosis can no longer use replacement estrogens, an issue that also affects younger breast cancer survivors as they enter menopause. Without estrogen replacement, the likelihood of sexual dysfunction increases.

An increasing percentage of women with breast cancer are receiving antiestrogenic therapy alone or in combination with chemotherapy. The data on the sexual side effects of these systemic treatments demonstrate a negative impact on sexual function. To treat these effects on sexual function atomoxetine can be administered alone or concurrent with antiestrogenic therapy, chemotherapy or a combination thereof.

The descriptions, best modes and treatment examples of the present invention are not intended to limit the scope of the invention. Various modifications, alternative constructions and equivalents may be employed without departing from the true spirit and scope of the invention.

What is claimed is:

1. A method for treating sexual dysfunction in a human in need thereof, said method comprising administering to the human an effective amount of atomoxetine or a pharmaceutically acceptable salt thereof, and a pharmaceutically acceptable carrier.

2. The method of claim 1 wherein the atomoxetine is atomoxetine HCl.

3. The method of claim 1 wherein the amount of atomoxetine is administered in an oral dose comprising about 10 milligrams to about 100 milligrams of atomoxetine per dose.

4. The method of claim 1 wherein the amount of atomoxetine is administered in a topical (sublingual or buccal) dose comprising about 10 milligrams to about 100 milligrams of atomoxetine per dose.

5. The method of claim 1 wherein atomoxetine is formulated in a dosage unit with a carrier that has a time release mechanism.

6. The method of claim 1 wherein atomoxetine is administered with a therapeutic having a mechanism of action different from atomoxetine.

7. The method of claim 1 wherein said human is a female.

8. The method of claim 1 wherein said human is a male.

9. The method of claim 1 wherein the sexual dysfunction is a sexual desire disorder.

10. The method of claim 1 wherein the sexual dysfunction is a sexual arousal disorder.

11. The method of claim 1 wherein the sexual dysfunction is an orgasmic disorder.

12. The method of claim 1 wherein the sexual dysfunction is premature ejaculation.

13. The method of claim 1 wherein the sexual dysfunction results from a general medical condition.

14. The method of claim 1 wherein the sexual dysfunction is induced by a substance.

* * * * *